(12) United States Patent
DeCarlo, Jr. et al.

(10) Patent No.: US 6,436,148 B1
(45) Date of Patent: Aug. 20, 2002

(54) IMPLANTABLE PROSTHESIS WITH BONE ENGAGING RIBS

(75) Inventors: Alfred F. DeCarlo, Jr., Stamford, CT (US); Bruce Khalili, Chestnut Hill, MA (US)

(73) Assignee: Depuy Orthopaedics, Inc., Warsaw, IN (US)

( * ) Notice: Subject to any disclaimer, the term of this patent is extended or adjusted under 35 U.S.C. 154(b) by 0 days.

(21) Appl. No.: 09/134,692

(22) Filed: Aug. 14, 1998

(51) Int. Cl.[7] ................................................. A61F 2/42
(52) U.S. Cl. ................................................. 623/23.15
(58) Field of Search ............................... 623/23, 23.11, 623/23.15, 22.4, 23.26, 23.31, 23.44, 23.48

(56) References Cited

U.S. PATENT DOCUMENTS

| | | | |
|---|---|---|---|
| 4,608,053 A | * 8/1986 | Keller | 623/23 |
| 4,623,349 A | * 11/1986 | Lord | 623/18 |
| 4,704,128 A | * 11/1987 | Frey | 623/23 |
| 4,728,334 A | * 3/1988 | Spotorno | 623/23 |
| 4,895,573 A | 1/1990 | Koeneman et al. | 623/23 |
| 5,222,985 A | 6/1993 | Homsy | 623/23 |
| 5,480,439 A | 1/1996 | Bisek et al. | 623/16 |
| 5,658,352 A | 8/1997 | Draenert | 623/23 |
| 5,702,461 A | 12/1997 | Pappas et al. | 623/20 |
| 5,755,805 A | 5/1998 | Whiteside | 623/22 |

FOREIGN PATENT DOCUMENTS

| | | | |
|---|---|---|---|
| EP | 222236 | * 10/1986 | 623/23 |
| EP | 499480 | * 8/1992 | 623/23 |
| EP | 0555613 | 8/1993 | A61F/2/36 |
| EP | 0720839 | 7/1996 | A61F/2/36 |
| FR | 2637494 | 4/1990 | A61F/2/32 |
| FR | 2667785 | * 4/1992 | 623/23 |
| FR | 2680315 | 2/1993 | A61F/2/36 |

* cited by examiner

Primary Examiner—David H. Willse
Assistant Examiner—Alvin Stewart
(74) Attorney, Agent, or Firm—Nutter, McClennen & Fish, LLP

(57) ABSTRACT

An implantable prosthetic component, such as a femoral stem, includes a plurality of bone-engaging ribs which are configured so as to engage dense cancellous bone upon implantation. The ribs have a geometry and spacing for achieving optimal fixation in the medullary canal of the femur by engaging predetermined dense cancellous bone.

20 Claims, 3 Drawing Sheets

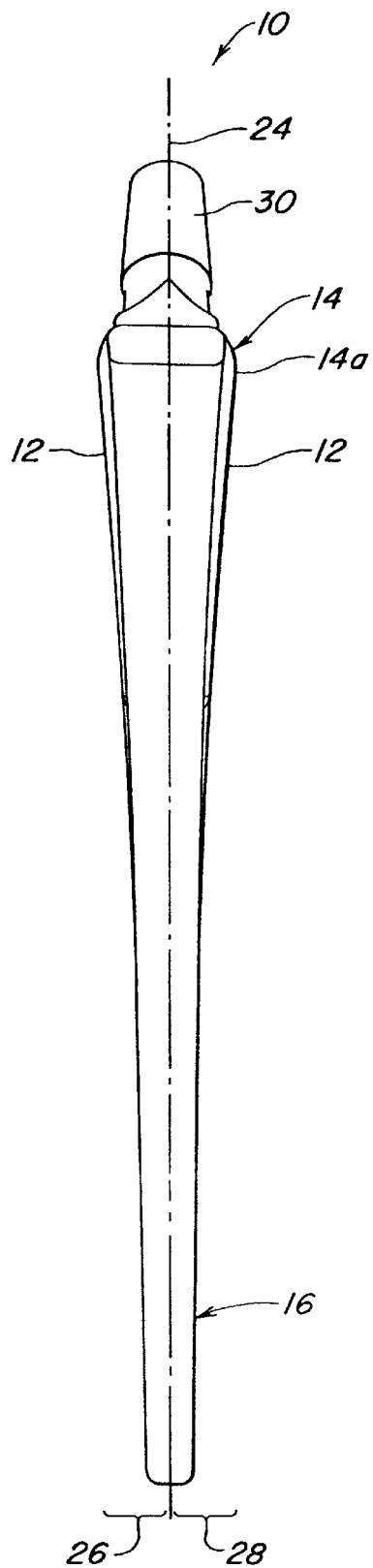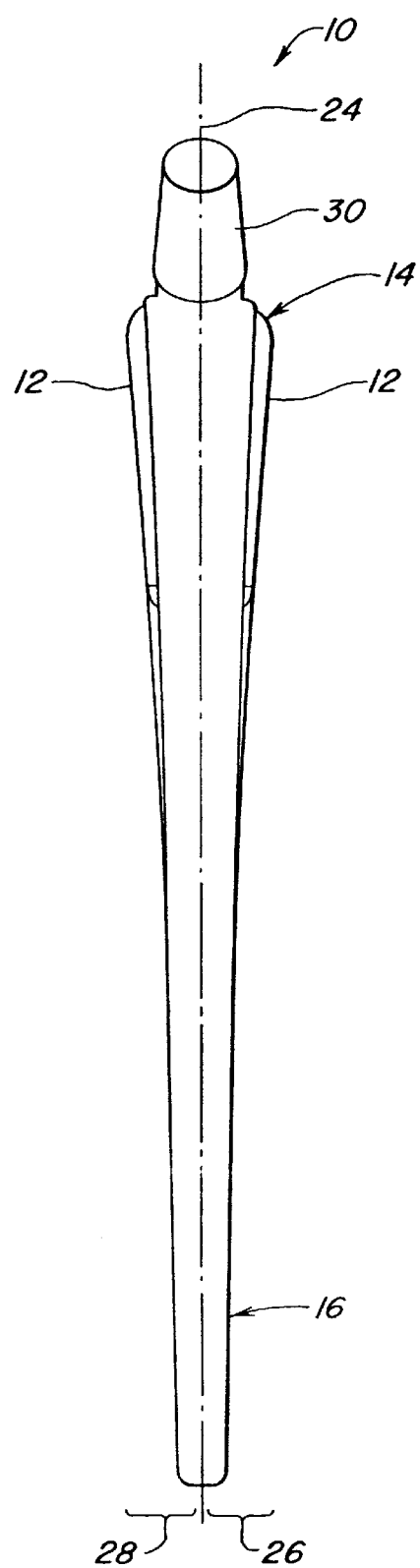
*FIG. 2*  *FIG. 3*

IMPLANTABLE PROSTHESIS WITH BONE ENGAGING RIBS

CROSS REFERENCE TO RELATED APPLICATIONS

Not Applicable.

STATEMENT REGARDING FEDERALLY SPONSORED RESEARCH

Not Applicable.

FIELD OF THE INVENTION

The present invention relates to joint prostheses, and more particularly, to joint prostheses which are implantable within the medullary canal of a bone.

BACKGROUND OF THE INVENTION

Joint arthroplasty is a well known surgical procedure by which a diseased and/or damaged natural joint is replaced with a prosthetic joint. Joint arthroplasty is commonly performed for hips, knees, elbows, and other joints. The health and condition of the natural joint to be replaced dictate the type of prosthesis needed for implantation. A hip arthroplasty refers to a surgical procedure where the natural femur is re-sectioned and a femoral component is implanted within the medullary canal. In a total hip arthroplasty, the natural acetabulum is replaced with an acetabular component which provides an articulation surface for the head of the femoral component.

Successful implantation of a femoral component requires adequate initial fixation and long term stability of the prosthetic component. One technique to secure the femoral component within the medullary canal includes the use of bone cement. It has been found, however, that known bone cements have certain drawbacks. For example, the implanted prosthesis can loosen over time and ultimately necessitate surgical revision of the implant.

Other attempts to enhance the fixation of a press-fit prosthetic component in the medullary canal include the use of various surface features formed on the implant, such as uniformly spaced flutes. While such surface features may provide some fixation to bone, the overall geometry of the prosthetic implant is not optimized for the available dense cancellous bone. For example, it is known that the most dense cancellous bone in the proximal portion of a femur is generally located on the anterior-lateral and postero-lateral portions of the femur. However, implants having evenly spaced ribs do not take into account a bone density gradient in the cancellous bone so that initial implant fixation is not optimized. Initial implant fixation is important to minimize motion between the bone and the implant so as allow bone ingrowth onto the implant surface which increases the likelihood of long term implant fixation.

Further, the contour of some femoral components is such that high quality, dense cancellous bone must be removed in order to accommodate the implant. This may result in the surface features being implanted within cancellous bone of lesser density than that which was removed. In addition, some implants are formed so as to conform to the cortical bone so that any surface features are positioned without regard to cancellous bone density.

It would, therefore, be desirable to provide a prosthetic component having surface features in the form of bone engaging ribs with a geometry for achieving optimal fixation in dense cancellous bone upon implantation into the medullary canal of a bone.

SUMMARY OF THE INVENTION

The present invention provides a joint prosthesis having an overall contour and surface geometry which optimize fixation properties. Although the invention is primarily shown and described as a femoral component of a hip prosthesis, it is understood that the invention is applicable to other joint prostheses as well.

In one embodiment, an artificial hip femoral component for implantation into the medullary canal of a femur includes a plurality of longitudinal, bone-engaging ribs formed on anterior and posterior surfaces of the femoral stem. The ribs are sized and spaced for optimal fixation within predetermined dense cancellous bone. A desirable geometry, spacing and number of ribs can be determined based upon a variety of factors, such as cancellous bone density profile and implant size. In one embodiment, at least three longitudinal ribs are formed on the surface of the stem with the spacing between adjacent ribs increasing in one direction. The ribs provide initial implant fixation, minimize micromotion of the implant, and facilitate load transfer from the implant to the bone.

BRIEF DESCRIPTION OF THE DRAWINGS

The invention will be more fully understood from the following detailed description taken in conjunction with the accompanying drawings, in which:

FIG. 2 is a lateral side view of the femoral component of FIG. 1;

FIG. 3 is a medial side view of the femoral component of FIG. 1;

DETAILED DESCRIPTION OF THE INVENTION

The drawings are understood to be illustrative of the concepts disclosed herein to facilitate an understanding of the invention. Further, the drawings are not necessarily to scale, and the scope of the invention is not to be limited by relative dimensions of the various features of the embodiments shown and described herein.

Figure 1:
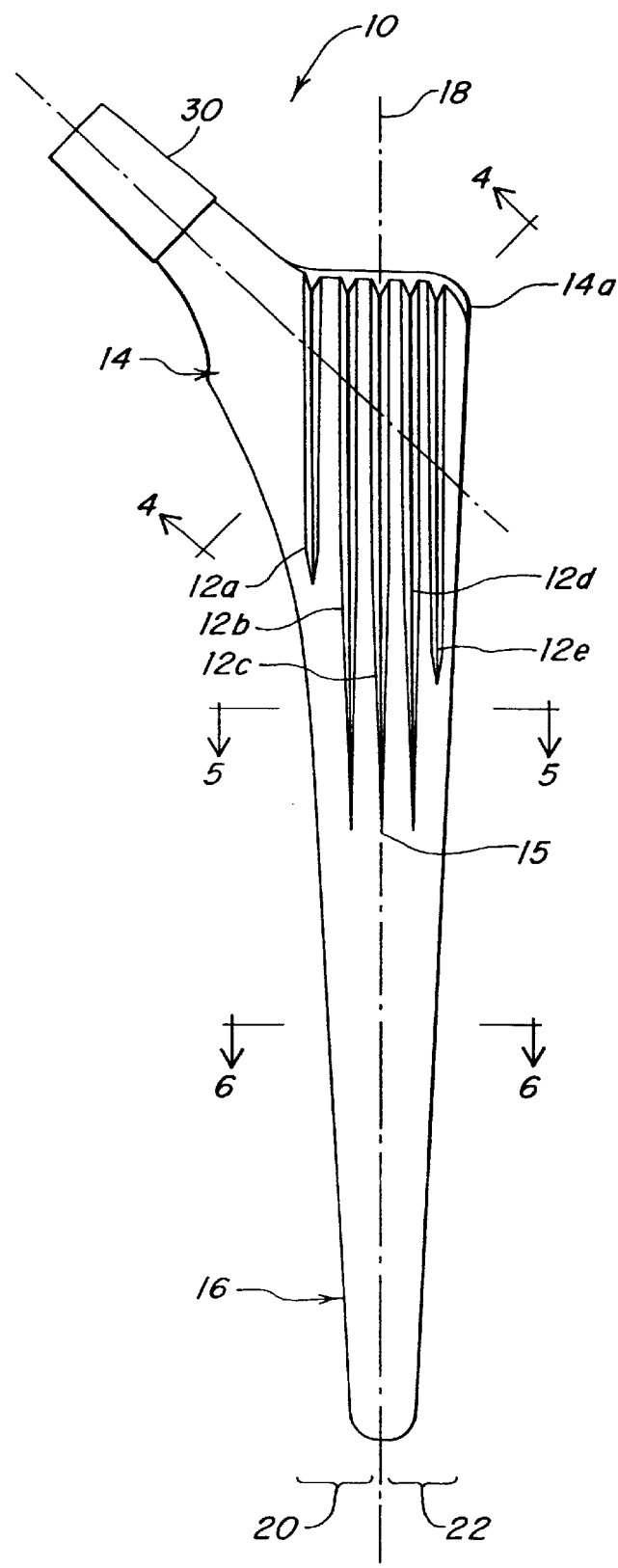
FIG. 1 is a front view of a hip prosthesis femoral component in accordance with the present invention.

FIG. 1 shows an exemplary embodiment of a hip prosthesis femoral component 10 having a plurality of bone-engaging ribs 12. The femoral component 10 is adapted for implantation into the medullary canal of a patient's femur. As described below, the ribs 12 are spaced and sized to optimize fixation within dense cancellous bone in the medullary canal of the femur. The overall geometry of the femoral component 10 optimizes contact between the ribs 12 and dense cancellous bone, the location of which can be predetermined.

It is understood that, as used herein, the relative locations and directions of medial, lateral, anterior and posterior are in reference to a human body. It is further understood that, when used in combination with a hip prosthesis femoral component, these terms refer generally to an orientation of the component after implantation in the patient. However, these terms are relative, and may be different for prosthetic components other than the hip prosthesis femoral component embodiments disclosed herein.

The femoral component or stem 10 has a superior or proximal portion 14 and an inferior or distal portion 16. A first plane 18 (FIG. 1) divides the femoral component 10 into medial and lateral portions 20,22 and a second plane 24 (FIG. 2) divides the stem 10 into anterior and posterior portions 26,28.

A neck 30 extends from the proximal portion 14 of the femoral component and is adapted for engagement with a head or ball (not shown). The head articulates in a natural acetabular cavity or a prosthetic acetabular component.

The ribs 12 are shown to be located generally on the proximal portion 14 of the femoral component 10 on both the anterior and posterior portions 26,28 of the stem. It is understood, however, that the ribs 12 can be formed on either or both of the anterior and posterior portions 26,28. It is further understood that ribs can be formed on the medial and/or lateral portions 20,22 of the femoral component 10. In addition, one or more of the ribs 12 can extend for virtually the entire length of the stem or for only a relatively small distance.

In general, the ribs 12 should extend longitudinally on the surface of the femoral component so as to correspond to the location of the most dense cancellous bone within the medullary canal in the femur. The location of the most dense cancellous bone in a patient's femur can be determined with the aid of a computed tomography (CT) or other system known to one of ordinary skill in the art. Such information can be used to customize the prosthesis for a given patient.

Figure 4:
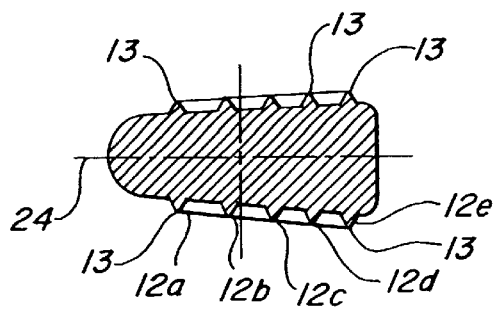
FIG. 4 is a cross-sectional view of the femoral component of FIG. 1 along line 4—4.
Figure 5:
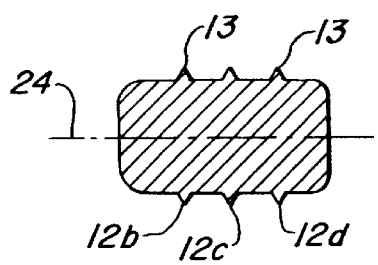
FIG. 5 is a cross-sectional view of the femoral component of FIG. 1 along line 5—5.
Figure 6:
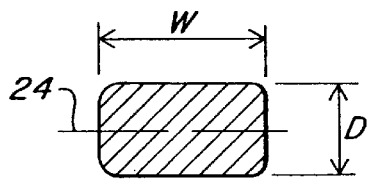
FIG. 6 is a cross-sectional view of the femoral component of FIG. 1 along line 6—6.

Accordingly, the geometry and the spacing of the ribs 12 can vary so as to optimize fixation within dense cancellous bone, allow effective load transfer to the bone and minimize micromotion of the implant with respect to the bone. The ribs 12 can have various cross-sectional geometries including triangles, quadrilaterals, and generally convex configurations, provided that the ribs include a bone-engaging edge 13. In addition, adjacent ribs can be generally parallel or they can be oriented so as to form a slight angle, i.e., less than about ten degrees. The edge 13 can be continuous or can be formed from discrete portions. Further, the edge 13 can be of a constant height, or it can taper or undulate in a pattern or in a random manner. It is understood that the term edge, as used herein, is intended to include a single crest as well as multiple crests. In the embodiments illustrated in FIGS. 1–8, and particularly in FIGS. 4–6, the ribs 12 have a triangular cross-section with an edge height that decreases in a distal direction.

Figure 8:
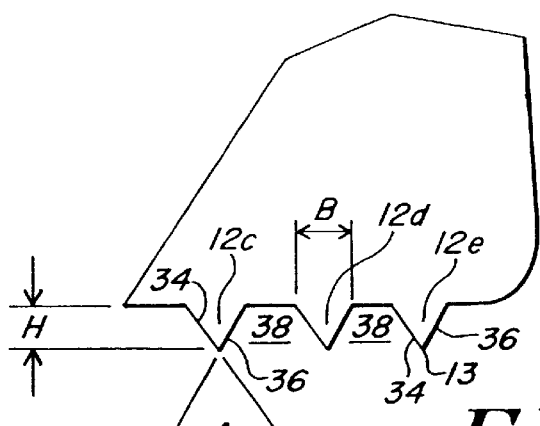
FIG. 8 is a more detailed view of a portion of the femoral component of FIG. 7 along line 8—8.

As shown in FIG. 8, each rib 12 has a medial surface 34 and a lateral surface 36 which intersect to form the edge or crest 13, and adjacent ribs 12 are separated by grooves 38. The edge 13 of the rib is effective to engage dense cancellous bone for allowing fixation of the femoral component within the medullary canal. It is understood that portions of the medial, lateral or groove surfaces can be textured so as to facilitate bone ingrowth.

One of ordinary skill in the art will appreciate that the ribs 12 can be defined by various parameters. For example, an angle A formed by the medial surface 34 and the lateral surface 36 can vary from about five degrees to about ninety degrees. The angle A can be optimized to minimize motion between the implant and the bone. In one embodiment, the angle A is about sixty degrees.

The height H of the ribs 12 can range from about one millimeter to about six millimeters. The height can be optimized to minimize movement of the implant without intruding into cortical bone. In one embodiment, the height H of the ribs 12 can vary along the length of the stem 10 to achieve the best fixation or contact with dense cancellous bone. Further, the height (H) can vary between adjacent ribs. In the embodiment shown in FIGS. 1–8, the height H is at a maximum near a proximal end 14a of the stem 10 and gradually decreases in a distal direction.

Figure 7:
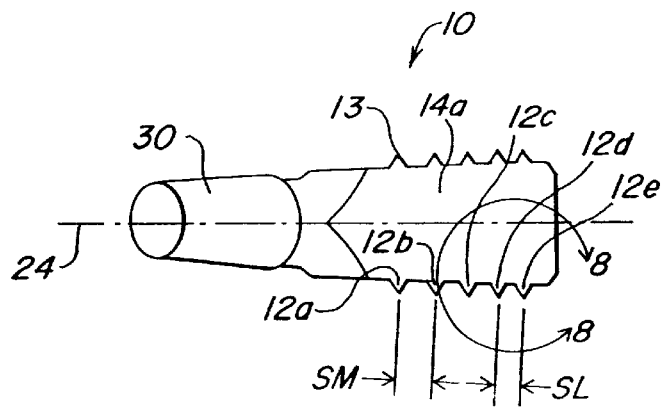
FIG. 7 is a top view of the femoral component of FIG. 1.

The spacing and number of ribs 12 formed on the stem 10 can also vary so as to optimize fixation within dense cancellous bone. As used herein, spacing refers to a distance between the edges 13 of adjacent ribs 12. In one embodiment, the spacing of adjacent ribs 12 increases in a medial direction. That is, the spacing SM between the medial ribs 12a,b is greater than the spacing SL between the lateral ribs 12c,d (FIG. 7). In an exemplary embodiment, the spacing of the ribs 12 can vary from about two millimeters to about seven millimeters.

The number of ribs 12 formed on the stem surface can vary depending upon a number of factors, such as bone density, implant size, and rib pitch. The number of ribs 12 can vary from three ribs to about seven ribs for relatively large femurs. In the embodiment shown in FIGS. 1–8, the femoral component 10 has five ribs 12a–e.

The length of the ribs 12 can also vary. In one embodiment, shown in FIGS. 1–8, five ribs 12a–e are formed on each of the anterior and posterior portions 26,28 of the stem 10. The three intermediate ribs 12b–d extend from the proximal end 14a of the stem to about the midpoint 15 of the stem and the medial-most and lateral-most ribs 12a, 12e extend for lesser distances. The medial-most rib 12a (FIG. 7) extends from the proximal end 14a to a point about one fourth the total stem length and the lateral-most rib 12e extends for about one third of the stem length. The length should be optimized to minimize the potential for cracking of the femur if the stem subsides and to allow maximum torsional load transfer from the stem to the bone.

It understood that the ribs formed on the anterior portion 26 of the stem 10 can be substantially symmetrical to ribs formed on the posterior portion 28 or they can be asymmetrical. Asymmetrical anterior/posterior rib spacing may be appropriate for optimizing fixation properties in differing bone densities. That is, ribs formed on the anterior portion 26 can be optimized for anterior cancellous bone having a first density and ribs formed on the posterior portion 28 can be optimized for posterior cancellous bone having a second density. In the embodiment of FIGS. 1–8, the anterior and posterior ribs are generally symmetrical.

Prior to implantation of a femoral stem in the patient's medullary canal, the patient's femur is examined with a CT scanning system to ascertain a density profile of the cancellous bone. For example, the bone density can be determined for the proximal one third of the femur at two millimeter frames. The outer contour and rib configuration of the femoral component 10 facilitate positioning of the bone-engaging ribs 12 within predetermined cancellous bone. By implanting the femoral component 10 and ribs 12 within the dense cancellous bone, optimal initial fixation, favorable load to bone transfer, and minimal micromotion are achieved. Optimal rib configuration should result in minimal micromotion at the bone/implant interface when under axial or torsional loading. Micromotion should be less than about fifty microinches to facilitate bone ingrowth.

In another embodiment, a prosthetic component system includes a plurality of components, such as femoral stems, each having a particular outer contour and rib configuration. The geometry of the femoral components can be based upon bone density information accumulated from the profiles of many patients. From this information, the various sized implants can be formed such that a selected one of the implants will provide optimal fixation properties for most patients. Thus, after performing a CT scan to obtain a bone density profile for a patient, an appropriate component is selected base on the bone density information and the bone size. The femur is prepared to receive the selected femoral stem so as to implant it within predetermined dense cancellous bone and achieve optimal fixation properties.

In one particular embodiment illustrated in FIGS. 1–8, the femoral component 10 has five ribs 12a–e formed thereon. The overall dimensions of the stem 10 include a length of about 170 millimeters, not including the neck 30. The width W (medial/lateral direction, FIG. 6) and depth D (anterior/posterior direction) of the stem increase from the distal tip of the stem 10 to the proximal end 14a. The width W is about 10 millimeters at the distal tip, about 16 millimeters at section 6—6, about 20 millimeters at section 5—5 and about 42 millimeters at section 4—4. The depth D is about 7 millimeters at the distal tip, about 9 millimeters at section 6—6, about 11 millimeters at section 5—5, and about 18 millimeters at section 4—4.

The five ribs 12 include three intermediate ribs 12b–d having a length of about 80 millimeters with the medial-most rib 12a having a length of about 40 millimeters and the lateral-most rib 12e having a length of about 55 millimeters. The ribs 12a–e extend from the proximal end 14a of the stem 10.

The ribs have a breadth B (FIG. 8) of about 2.0 millimeters proximate section 4—4. The breadth B gradually decreases to about 0.5 millimeter at section 5—5. This allows for maximum torsional load transfer for proximal loads which reduces the potential for proximal bone resorption thereby increasing the likelihood of long-term implant fixation.

The spacing of adjacent ribs 12 increases in a medial direction such that, as measured edge to edge, adjacent ribs have spacings of about 5.1 millimeters (12a,b), about 4.8 millimeters (12b,c), about 4.3 millimeters (12c,d), and about 3.8 millimeters (12d,e). The height H of the ribs 12 is about 1.7 millimeter.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. An implantable prosthetic component, comprising:
   an elongate body having a surface and a longitudinal axis; and
   a plurality of ribs protruding above the surface of the body as positive surface features to engage bone and extending in a direction substantially parallel to the longitudinal axis of the body, the plurality of ribs including
   a first rib;
   a second rib adjacent to the first rib; and
   a third rib adjacent to the second rib such that a first spacing between the first and second ribs is greater than a second spacing between the second and third ribs.

2. The prosthetic component according to claim 1, wherein the first and second ribs are parallel to one another.

3. The prosthetic component according to claim 1, wherein the first and second ribs differ in length.

4. The prosthetic component according to claim 1, wherein the prosthetic component is a femoral component of a hip prosthesis.

5. The prosthetic component according to claim 4, wherein the second rib is lateral to the first rib.

6. The prosthetic component according to claim 1, wherein the first and second spacing varies from about four millimeters to about six millimeters.

7. The prosthetic component according to claim 1, wherein each of the plurality of ribs has a bone-engaging edge that is formed by a peak of the rib.

8. The prosthetic component according to claim 7, wherein the edge has a height that decreases along a length of the prosthetic component.

9. The prosthetic component according to claim 8, wherein the height decreases from a proximal end to a distal end thereof.

10. The prosthetic component according to claim 1, wherein each of the plurality of ribs has a height in the range from about 0.5 millimeter to about 5.0 millimeters.

11. The prosthetic component according to claim 1, wherein the first rib has a height that differs from that of the second rib.

12. The prosthetic component according to claim 1, wherein each of the plurality of ribs has a generally triangular cross-section.

13. The prosthetic component according to claim 10, wherein the plurality of ribs further includes fourth and fifth ribs, wherein at least one of the first, second, third, fourth and fifth ribs extends from one end of the body to a point about one half a total length of the body.

14. The prosthetic component according to claim 1, wherein the prosthetic component is a femoral component of a hip prosthesis and the ribs are formed on and protrude above an anterior portion of the body.

15. The prosthetic component according to claim 14, wherein further ribs are formed on and protrude above a posterior portion of the body.

16. A hip prosthesis femoral stem component, comprising:
   a stem having a proximal end and a distal end, a longitudinal axis, and a posterior side and an anterior side; and
   a first plurality of generally parallel ribs formed along and protruding above the surface of a portion of a length of the anterior side of the stem in a direction substantially parallel to the longitudinal axis of the stem, such that a spacing between adjacent ones of the plurality of ribs increases in a medial direction.

17. The femoral stem component according to claim 16, further including a second plurality of ribs formed on and protruding above the surface of a posterior side of the stem, the second plurality of ribs extending in a direction substantially parallel to the longitudinal axis of the stem.

18. The femoral stem component according to claim 17, wherein adjacent ones of the second plurality of ribs have a spacing that increases in the medial direction.

19. The femoral stem component according to claim 17, wherein the first and second plurality of ribs are generally symmetrical.

20. The femoral stem component according to claim 17, wherein the first and second plurality of ribs are generally asymmetrical.

* * * * *